United States Patent [19]

Tatee et al.

[11] Patent Number: 5,245,052
[45] Date of Patent: Sep. 14, 1993

[54] PROCESS FOR PRODUCING 6-ACYL-7-DEACETYLFORSKOLIN DERIVATIVES

[75] Inventors: Tochiro Tatee, Tokyo; Tatsuo Sugioka, Saitama, both of Japan

[73] Assignees: Nippon Kayaku Co. Ltd.; Hoechst Japan Limited, both of Tokyo, Japan

[21] Appl. No.: 732,547

[22] Filed: Jul. 19, 1991

[30] Foreign Application Priority Data

Jul. 23, 1990 [JP] Japan .................. 2-194562

[51] Int. Cl.$^5$ .......................... C07D 311/92
[52] U.S. Cl. ................................. 549/389
[58] Field of Search .......................... 549/389

[56] References Cited

FOREIGN PATENT DOCUMENTS

| 0222413 | 5/1987 | European Pat. Off. |  |
|---------|--------|-------------------|--------|
| 0297496 | 1/1989 | European Pat. Off. | 549/389 |
| 0341571 | 11/1989 | European Pat. Off. | 549/389 |
| 0009986 | 1/1989 | Japan | 549/389 |

*Primary Examiner*—C. Warren Ivy
*Assistant Examiner*—A. Owens
*Attorney, Agent, or Firm*—Finnegan, Henderson, Farabow, Garrett & Dunner

[57] ABSTRACT

A process for the manufacture of a 6-acyl-7-deacetylforskolin derivative represented by formula (I)

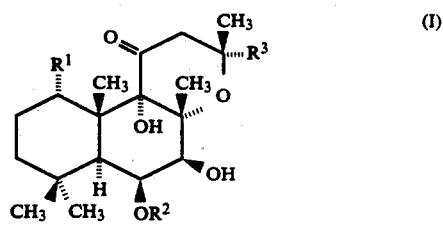

by reacting a 7-acyl-7-deacetylforskolin derivative represented by formula (II)

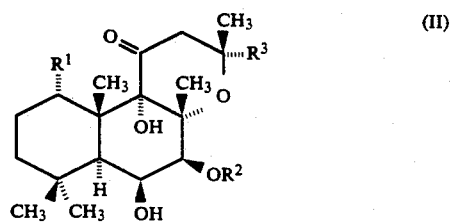

with a strong base in an aprotic solvent.

6 Claims, No Drawings

PROCESS FOR PRODUCING 6-ACYL-7-DEACETYLFORSKOLIN DERIVATIVES

BACKGROUND OF THE INVENTION

1. Field of the Invention

This invention relates to a novel process for producing 6-acyl-7-deacetylforskolin derivatives expectedly useful as medical drugs.

2. Description of Prior Arts

As process for producing 6-acyl -7-deacetylforskolin, a process which comprises reacting 7-acyl-7-deacetylforskolin with sodium hydroxide in a protonic solvent at ambient temperature and thereby rearranging the 7-acyl group to the 6-position is known (Japanese Patent Application Kokai (Laid-Open) No. 63-10783), for example.

However, the process mentioned above is unsuitable for large scale synthesis in that it yields 7-deacetylforskolin as a by-product formed by hydrolysis of starting compound, which lowers the yield of main product and complicates the procedure o purification because the by-product can be removed only by chromatography.

SUMMARY OF THE INVENTION

Thus, after many studies, the present inventors found that, by merely reacting a strong base such as methyllithium or the like upon a 7-acyl-7-deacetylforskolin derivative represented by the following formula (II):

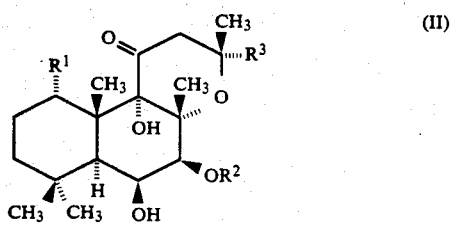

(wherein $R^1$ represents an optionally esterified, etherified or silylated hydroxyl group, $R^2$ represents an acyl group, and $R^3$ represents a hydrocarbon group having 2 to 3 carbon atoms) in an aprotic solvent, the 7-acyl group is rearranged into the 6-position and a rearranged product, i.e. 6-acyl-7-deacetylforskolin derivative represented by the following formula (I):

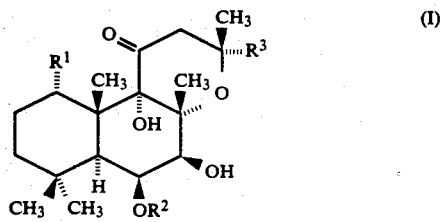

(wherein $R^1$, $R^2$ and $R^3$ are as defined above) is obtained without formation of hydrolyzate. Further, it was also found that the process of this invention gives the rearranged product in a high yield even when $R^2$ is sterically bulky group such as benzoyl group nd the like. This invention was accomplished based on the above-mentioned findings.

DESCRIPTION OF THE PREFERRED EMBODIMENTS

In general formulas (I) and (II) mentioned above, $R^1$ is a hydroxyl group which may optionally be esterified, etherified or silylated. Its examples include hydroxyl group; acyloxy groups such as formyloxy, acetoxy, propionyloxy, butyryloxy, benzoyloxy, 4-methoxybenzoyloxy, dimethylaminoacetoxy, piperidinoacetoxy, diethylaminoacetoxy, morpholinoacetoxy, (4-hydroxypiperidino)acetoxy, dipropylaminoacetoxy, 2-ethylaminopropionyloxy, thiomorpholinoacetoxy, 2-morpholinopropionyloxy, isopropylaminoacetoxy, 2-dimethylaminopropionyloxy, t-butylaminoacetoxy, 3-dimethylaminopropionyloxy, (4-methylpiperazino)-acetoxy, 2-dimethylaminobutyryloxy, 3-dimethylaminobutyryloxy, 4-dimethylaminobutyryloxy, glycoloyloxy, 2, 3-dihydroxypropionyloxy, thioglycoloyloxy, hemisuccinyloxy, hemiglutaryloxy, glycyloxy, 2-aminopropionyloxy, 3-aminopropionyloxy, 2-methylaminobutyryloxy, nicotinoyloxy, furoyloxy, histidyloxy, lysyloxy and the like; silyloxy groups such as trimethylsilyloxy t-butyldiphenylsilyloxy, t-butyldimethylsilyloxy and the like; substituted alkoxy groups such as 2-methoxyethoxymethoxy, methoxy, methylthiomethoxy, methoxymethoxy, benzyloxy and the like; substituted alkoxycarbonyloxy groups such as benzyloxycarbonyloxy, t-butoxycarbonyloxy and the like; etc.

$R^2$ is an acyl group, of which examples include formyl, acetyl, propionyl, butyryl, dimethylaminoacetyl, butylaminoacetyl, diethylaminoacetyl, pyrrolidinoacetyl, piperazinoacetyl, morpholinoacetyl, piperidinoacetyl, N-cyclohexyl-N-methylaminoacetyl, (4-methylpiperazino)-acetyl, dipropylaminoacetyl, (4-hydroxypiperidino)-acetyl, thiomorpholinoacetyl, isopropylaminoacetyl, t-butylaminoacetyl, glycyl, benzyloxycarbonylaminoacetyl, 2-aminopropionyl, 3-aminopropionyl, 2-dimethylaminopropionyl, 3-dimethylaminopropionyl, 2-pyrrolidinopropionyl, 3-piperazinopropionyl, 2-butylamino-propionyl, 3-diethylaminopropionyl, 2-morpholinopropionyl, 3-piperidinopropionyl, 3-(t-butoxycarbonylamino)-propionyl, 2-aminobutyryl, 3-aminobutyryl, 4-dimethylaminobutyryl, 4-aminobutyryl, 2-dimethylaminobutyryl, 3-diethylaminobutyryl, 4-isopropylaminobutyryl, 2-butylaminobutyryl, 3-pyrrolidinobutyryl, 4-morpholinobutyryl, 2-piperazinobutyryl, 3-piperidinobutyryl, 4-thiomorpholinobutyryl, 2-aminopentanoyl, 3-dimethylaminopentanoyl, 4-diethylaminopentanoyl, 5-pyrrolidinopentanoyl, 2-piperidinohexanoyl, 3-morpholinohexanoyl, 4-(4-methylpiperazino)-hexanoyl, 5-(t-butylamino)-hexanoyl, 6-methylaminohexanoyl, 3-dimethylamino-2-methylpropionyl, 3-pyrrolidino-2-methylpropionyl, 3-dimethylamino-2-ethylpropionyl, 4-dimethylamino-2-methylbutyryl, 4-amino-2-propylbutyryl, hemisuccinyl, hemiglutaryl, thioglycoloyl, thienoyl, isonicotinoyl, prolyl, histidyl, lysyl, tyrosyl, methionyl, ornithyl, glycoloyl, lactoyl and 2, 3-dihydroxypropionyl groups, and benzoyl groups optionally having substituent(s) on benzene ring such as benzoyl, p-bromobenzoyl, p-chlorobenzoyl, p-iodobenzoyl, p-methoxybenzoyl, p-dimethylaminobenzoyl, m-bromobenzoyl, o-chlorobenzoyl, m-iodobenzoyl, o-methoxybenzoyl, m-dimethylaminobenzoyl and the like.

Examples of $R^3$ include hydrocarbon groups having 2-3 carbon atoms such as vinyl, ethyl, cyclopropyl and the like.

Examples of the compound of general formula (II) include:

7-deacetyl-7-dimethylaminoacetylforskolin,
7-deacetyl-7-glycylforskolin,
7-deacetyl-7-piperidinoacetylforskolin,
7-deacetyl-7-(2-dimethylaminopropionyl)-forskolin,
7-deactyl-7-(3-dimethylaminopropionyl)-forskolin,
7-deacetyl-7-(2-morpholinopropionyl)-forskolin,
7-deacetyl-7-alanylforskolin,
7-deacetyl-7-(2-aminobutyryl)-forskolin,
7-deacetyl-7-(4-dimethylaminobutyryl)-forskolin,
7-deacetyl-7-(2, 3-dihydroxypropionyl)-forskolin,
7-deacetyl-7-hemisuccinylforskolin,
7-deacetyl-7-histidylforskolin,
7-deacetyl-7-prolylforskolin,
7-deacetyl-7-lysylforskolin,
7-deacetyl-7-glycoloylforskolin,
7-deacetyl-14, 15-dihydro-7-dimethylaminoacetylforskolin,
7-deacetyl-14, 15-dihydro-7-(3-dimethylaminopropionyl)-forskolin,
7-deacetyl-14, 15-dihydro-7-(4-dimethylaminobutyryl)-forskolin,
13-cyclopropyl-7-deacetyl-7-(3-dimethylaminopropionyl)-14, 15-dinorforskolin,
13-cyclopropyl-7-deacetyl-7-(4-dimethylaminobutyryl)-14, 15-dinorforskolin,
7-deacetyl-14, 15-dihydro-7-pyrrolidinoacetylforskolin,
7-deacetyl-14, 15-dihydro-7-(2-morpholinopropionyl)-forskolin,
1-acetylforskolin,
1-t-butyldimethylsilylforskolin,
1-benzoylforskolin,
1-benzylforskolin,
1-methoxyforskolin,
1-trimethylsilylforskolin,
1-t-butyldiphenylsilylforskolin,
1-(2-methoxyethoxymethyl)-forskolin,
1-methylthiomethylforskolin,
1-methoxymethylforskolin,
1-benzyloxycarbonylforskolin,
1-(t-butoxycarbonyl)-forskolin,
1-acetyl-7-deacetyl-7-propionylforskolin,
1-t-butyldimethylsilyl-7-butyryl-7-deacetylforskolin,
1-benzyl-7-deacetyl-7-pentanoylforskolin,
1-(2-methoxyethoxymethyl)-forskolin,
1-benzoyl-14, 15-dihydroforskolin,
14, 15-dihydro-1-trimethylsilylforskolin,
1-methoxy-14, 15-dihydro-7-deacetyl-7-propionylforskolin,
1-t-butyldiphenylsilyl-13-cyclopropyl-14, 15-dinor-7-deacetyl-7-butyrylforskolin,
1-benzyloxy-13-cyclopropyl-14, 15-dinor-7-deacetyl-7-(3-dimethylpropionyl)-forskolin,
1-(t-butoxycarbonyl)-13-cyclopropyl-14, 15-dinor-7-deacetyl-7-(4-dimethylbutyryl)-forskolin,
1-methylthiomethyl-13-cyclopropyl-14, 15-dinor-7-deacetyl-7-methylaminoacetylforskolin,
14, 15-dihydroforskolin,
13-cyclopropyl-14, 15-dinorforskolin,
7-deacetylforskolin-7-(2, 2-dimethyl-1, 3-dioxolan-4-carboxylate),
7-deacetyl-7-(3-dimethylamino-2-methylpropionyl)-forskolin,
14, 15-dihydro-7-deacetyl-7-(3-dimethylamino-2-methylpropionyl)-forskolin,
7-deacetyl-7-(4-dimethylamino-2-methylbutyryl)-forskolin,
14, 15-dihydro-7-deacetyl-7-(4-dimethylamino-2-methybutyryl)-forskolin,
7-benzoyl-7-deacetylforskolin,
7-(p-bromobenzoyl)-7-deacetylforskolin,
7-(p-cholorobenzoyl)-7-deacetylforskolin,
7-(p-iodobenzoyl)-7-deacetylforskolin,
7-(p-methoxybenzoyl)-7-deacetylforskolin,
7-(p-dimethylaminobenzoyl)-7-deacetylforskolin,
7-(m-bromobenzoyl)-7-deacetylforskolin,
7-(o-cholorobenzoyl)-7-deacetylforskolin,
7-(m-iodobenzoyl)-7-deacetylforskolin,
7-(o-methoxybenzoyl)-7-deacetylforskolin,
7-(m-dimethylaminobenzoyl)-7-deacetylforskolin, and the like.

In this invention, the reaction temperature ranges from −80° C. to boiling point of the solvent, preferably from −80° C. to 0° C., and more preferably from −50° C. to −70° C.

Though the reaction time varies with the temperature, it usually one minute or longer, and preferably about 30 minutes to out 12 hours.

As the aprotic solvent, hexane, benzene, toluene, xylene, diethyl ether, diisopropyl ether, tetrahydrofuran, dioxane, diglyme, triglyme and the like are preferably used.

As the strong base, organometals, metal hydrides and metal amides are preferred. As the metal, alkali metals and alkaline earth metals are preferred. Examples of preferably usable base include methyllithium, ethyllithium, butyllithium, phenyllithium, lithium-bis (trimethylsilyl) amide, lithium amide, sodium amide, potassium amide, lithium hydride, sodium hydride, potassium hydride, methylmagnesium iodide, ethylmagnesium bromide, phenylmagnesium bromide, phenylmagnesium iodide, lithium dicyclohexylamide, lithium diisopropylamide and the like. The base used in an amount of about 0.1-10 times as expressed in terms of molar ratio.

According to this invention, the 7-acyl group of forskolins can be rearranged to 6-position readily and in a high yield, and thereby 6-acyl derivatives of forskolin having a high purity can be obtained.

EXAMPLE 1:
7-DEACTYL-6-(3-DIMETHYLAMINOPROPIONYL)-FORSKOLIN

7-Deacetyl-7-(3-dimethylaminopropionyl)-forskolin (200 mg) was dissolved into anhydrous tetrahydrofuran, to which was added 5 ml of a 0.98M solution of methyllithium in diethyl ether under a stream of nitrogen gas at a temperature of −78° C. in an atmosphere of nitrogen gas. Stirring was continued for an additional 6 hours at −78° C. in an atmosphere of nitrogen gas. After the reaction, 10% aqueous solution of ammonium chloride was added. The resulting mixture was diluted with saturated aqueous solution of sodium chloride and extracted with ethyl acetate. The organic layer was washed with water and dried on magnesium sulfate, the drying agent was filtered off, and the filtrate was concentrated. The concentrate (216.5 mg) was poured into a silica gel chromatographic column (30 g) and eluted with dichloromethanemethanol mixture (30:1) to obtain 7-deacetyl-6-(3-dimethylaminopropionyl)-forskolin (112 mg, yield 56%). The unreacted 7-deacetyl-7-(3-dimethylaminopropionyl)-forskolin (75 mg) was similarly reacted and purified by chromatography to obtain 7-deactyl-6-(3-dimethylaminopropionyl)-forskolin in an additional yield of 43 mg. The total yield was 78%.

EXAMPLE 2:
6-(P-BROMOBENZOYL)-7-DEACTYLFORSKOLIN

While cooling a mixture consisting of 7-deacetyl-7-(p-bromobenzoyl)-forskolin (320 mg) and tetrahydrofuran (10 ml) at −78° C., 1 ml of a 1.4M solution of methyllithium in ethyl ether was added thereto, and the resulting mixture was stirred for 30 minutes. After the reaction, the reaction mixture was poured into an aqueous solution of ammonium chloride and extracted with ethyl acetate. The organic layer was washed with water and dried on anhydrous sodium sulfate, after which the drying agent was filtered off. The filtrate was concentrated under reduced pressure and the residue was recrystallized from ethyl ether-petroleum ether mixture to obtain 6-(p-bromobenzoyl)-7-deactylforskolin (290 mg().

IR (KBr) ν: 3573, 3259, 2944, 1726, 1707, 1589, 1398, 1270, 1101, 1012, 754 cm$^{-1}$.

$^1$H-NMR (CDCl$_3$) δ: 0.94 (3H, s), 1.11 (3H, s), 1.40 (3H, s), 1.55 (3H, s), 1.64 (3 H, s), 2.45 (1H, d, J=3.1 Hz), 2.52 (1H, d, J=17 Hz), 3.23 (1H, d, J=17 Hz), 4.41 (1H, d, J=4.8 Hz), 4.65~4.80 (1H, m), 5.0 (1H, dd, J=10.6, 1.1 Hz), 5.19 (1H, J=17, 1.1 Hz), 6.14 (IH, dd, J=17.4, 10.5 Hz), 6.17 (1H, dd, J=4.8, 3.1 Hz), 7.5–7.7 (2H, m), 7.8~8.0 (2H, m).

What is claimed is:

1. A process for producing a 6-acyl-7-deactylforskolin derivative represented by formula (I):

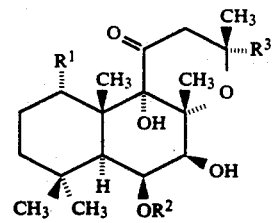

wherein R$^1$ represents an optionally esterified, etherified or silylated hydroxyl group, R$^2$ represents an acyl group and R$^3$ represents a hydrocarbon group having 2 to 3 carbon atoms, which comprises reacting a 7-acyl-7-deactylforskolin derivative represented by formula (II):

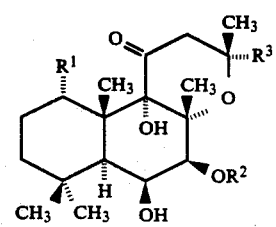

where R$^1$, R$^2$ and R$^3$ are as defined above, with an organometallic compound or metal amide, in which the metal in the organometallic compound or metal amide is an alkali metal or an alkaline earth metal, in an anhydrous aprotic solvent.

2. The process of claim 1, wherein the organometallic compound or metal amide is methyllithium.

3. The process of claim 1, wherein the anhydrous aprotic solvent is anhydrous tetrahydrofuran.

4. The process of claim 1, wherein the reaction occurs at a temperature from −80° C. to the boiling point of the solvent.

5. The process of claim 1, wherein the reaction occurs at a temperature from −80° C. to 0° C.

6. The process of claim 1, wherein the reaction occurs at a temperature from −50° C. to −70° C.

* * * * *